United States Patent [19]

Chu et al.

[11] Patent Number: 5,583,225
[45] Date of Patent: Dec. 10, 1996

[54] SYNTHESES OF ACYCLIC GUANINE NUCLEOSIDES

[75] Inventors: Chung K. Chu; Jinfa Du, both of Athens, Ga.

[73] Assignee: University of Georgia Research Foundation, Inc., Athens, Ga.

[21] Appl. No.: 245,024

[22] Filed: May 17, 1994

[51] Int. Cl.[6] .................................................. C07D 473/18
[52] U.S. Cl. ............................................................ 544/276
[58] Field of Search ............................................. 544/276

[56] References Cited

U.S. PATENT DOCUMENTS 5,336,770  8/1994  Shiragami .................. 544/276

FOREIGN PATENT DOCUMENTS

0165164A1  12/1985  European Pat. Off. .

OTHER PUBLICATIONS

Boryski, Nucleosides & Nucleotides 6, 385 (1987).
Boryski, Nucleosides & Nucleotides 8, 529 (1989).
Acton, E. M. et al., "The Mercury Salt of 2–Acetamido–6–chloropurine," *Synthetic Procedures in Nucleic Acid Chemistry* 1968, 1, 25–27.
Chen et al., "An Improved Synthesis of Acyclovir," CA 117:151269e (1992).
Field, A. K. et al., "9{[2–Hydroxyl–1–(hydroxymethyl)ethoxy]methyl}guanine: A selective inhibitor of herpes group virus replication," *Proc. Natl. Acad. Sci.* : USA, 1983, 80 4139–4143.
Hakimelahi, G. H., et al., "Catalytic Effect of Tetrabutylammonium Fluoride in the Preparation of Secoribo–nucleosides," *Helv. Chim.* 1989, 72, 1495–1500.

Martin J. C. et al., "9–[(1,3–Dihydroxy–2–propoxy)methyl] guanine: A New Potent and Selective Antiherpes Agent," *J. Med. Chem.* 1983, 26(5), 759–761.
Matsumoto, H. et al., "A Convenient Synthesis of 9–(2–Hydroxyethoxy–methyl)guanine (Acyclovir) and Related Compounds," *Chem. Pharm. Bull.* 1988, 36 (3), 1153–1157.
Ogilivie, K. K. et al., "Biologically active acyclonucleoside analogues. II. The Synthesis of 9–[(2–hydroxy–1–(hydroxymethyl)ethoxyl]methyl] guanine (BIOLF–62)," *Can. J. Chem.* 1982, 60, 3005–3010.
Schaeffer, H. J. et al., "9–(2–Hydroxyethoxymethyl)guanine activity against viruses of the herpes group," *Nature* 1978 (London), 272, 583–585.
Zou et al., "High–yield regioselective synthesis of 9–glycosyl guanine nucleosides and analogues via coupling with 2–N–acetyl–6–O–diphenylcarbamoylguanine," *Can. J. Chem.* 1987, 65, 1436–1437.

*Primary Examiner*—Mark L. Berch
*Attorney, Agent, or Firm*—Cheryl K. Zalesky; Kilpatrick & Cody

[57] ABSTRACT

A method is provided for the synthesis of synthesis of acyclic purine nucleosides, particularly 9-(2-hydroxyethoxymethyl)-guanine (acyclovir) and 9-[(1,3-dihydroxy-2-propoxy)methyl]guanine ("DHPG") where the $N^2,N^9$-diprotected guanine is reacted with $CH_3C(O)OCH_2O(CH_2)_2)OC(O)CH_3$ or diacetoxypropane, respectively, in the presence of a mixture of an acid and acetic anhydride, or in the presence of an acid, where the acid can be phosphoric acid or polyphosphoric acid.

13 Claims, 2 Drawing Sheets

SYNTHESES OF ACYCLIC GUANINE NUCLEOSIDES

FIELD OF THE INVENTION

This invention is in the area of organic chemistry, and in particular provides a synthesis of acyclic purine nucleosides, including 9-(2-hydroxyethoxymethyl)-guanine (acyclovir) and 9-[(1,3-dihydroxy-2-propoxy)methyl]guanine ("DHPG").

BACKGROUND OF THE INVENTION

Guanine, illustrated below, is one the five heterocyclic bases commonly found in DNA and RNA. Guanine is a particularly difficult base to work with because coupling of the base with electrophilic reagents usually results in $N^7/N^9$ isomeric mixtures that are frequently difficult to separate and result in decreased yields.

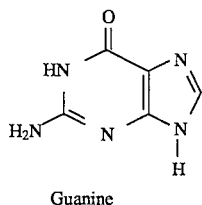

Guanine

An acyclic nucleoside is one that contains a non-cyclic carbohydrate or carbohydrate-type group attached to the purine or pyrimidine base. Two guanine-containing acyclic nucleosides that are currently used therapeutically for the treatment of viruses are 9-(2-hydroxyethoxymethyl)-guanine (acyclovir) and 9-[(1,3-dihydroxy-2-propoxy)methyl]guanine ("DHPG").

Acyclovir, illustrated below, is administered therapeutically for the treatment of herpes simplex virus (types 1 and 2) and varicella zoster virus (herpes zoster and chicken pox). H. J. Schaeffer. et al. *Nature* (London). 1978, 272, 583; Martindale, *The Extra Pharmacopoeia*, Twenty-ninth Edition, The Pharmaceutical Press (1989).

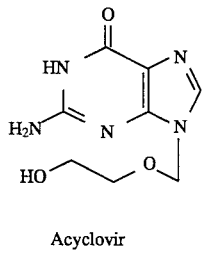

Acyclovir

Discovery of the potent activity of acyclovir led to many efforts to synthesize the compound. A number of schemes have been proposed or used. One method involves the condensation of silylated guanine with 2-benzoxyethoxymethyl chloride in the presence of $Bu_4NF$ as a catalyst to give exclusively the $N^9$-substituted product. G. H. Hakimelahi. et al. *Helv. Chim.* 1989, 72, 1495.

Chen et al., *J. China Pharm. Univ.* 1992, 23(1), 43, prepared acyclovir by reacting diacetylguanine with dioxolane in the presence of p-toluenesulfonic acid. The product was a syrup containing a mixture of $N^9/N^7$-isomers in which the ratio of $N^9/N^7$-isomers was about 3/2 in favor of the $N^9$-isomer. Contrary to the article, however, the present inventors did not observe any significant amount of $N^9$-isomer precipitating from this syrup after treatment with chloroform.

Matsumoto, et al., have studied the effect of solvent, acid catalyst and reaction temperature on yield of the alkylation of diacetylguanine with 2-oxo-1,4-butanediol diacetate ("dioxolane diacetate") to produce $N^2$,O-diacetylacyclovir. H. Matsumoto. et al. *Chem. Pharm. Bull.* 1988, 36 (3), 1153. Of the acid catalysts tested (p-toluenesulfonic acid, sulfanilic acid, p-nitrobenzenesulfonic acid, 2,4-dinitrobenzene sulfonic acid, iron(II) sulfate, and zinc chloride), Matsumoto reported that p-toluenesulfonic acid and sulfanilic acid exhibited the highest catalytic activity. The Matsumoto method provides a mixture of $N^9$- and $N^7$-substituted compounds which had to be separated. Matsumoto deprotected $N^2$,O-diacetylacyclovir with methanol saturated with ammonia, to provide an overall yield of acyclovir of 43%. O-Acetylacyclovir was obtained when methanolic methoxide was used, and $N^2$-acetylacyclovir was obtained when aqueous ammonium hydroxide was used. Matsumoto reported that DMSO was the solvent of choice for the reaction.

Diacetylguanine, which has been used as an intermediate in the production of acyclovir, has been prepared using several methods. Guanine has been acetylated using acetic anhydride in N,N-dimethylacetamide to give diacetylguanine in 90.5% yield. M. J. Robins. *Can.J.Chem.* 1987, 65, 1436. This reaction produces a product which is grey in color due to the high reaction temperature used (160° C. for 7 hours).

Guanine has also been acetylated in acetic anhydride and acetic acid to give different products depending on the workup conditions. H. Matsumoto. et al. *Chem.Pharm.Bull.* 1988, 36 (3), 1153. For example, after the reaction mixture becomes an almost clear solution, if solvents are removed by distillation, only diacetyl guanine is obtained in 95% yield. However, the addition of water at 60° C. followed by stirring at room temperature overnight produces $N^2$-acetylguanine in 94.4% yield. If the reaction mixture is merely cooled down, a mixture of mono- and di-acetylguanine is produced.

2-Amino-6-chloropurine has been acetylated in acetic anhydride in the presence of phosphoric acid. E. M. Acton, R. H. Iwamoto, *Synthetic Procedures in Nucleic Acid Chemistry*. 1968, 1, 25. The reaction produced di- and tri-acetylated products in forty minutes. However, the acetylation of guanine under these conditions required more catalyst (8.4%) and a longer reaction time (3 hours) than 2-amino-6-chloropurine. During the reaction, the acetylated guanine became deep brown, and the coloration was difficult to remove.

9-[(1,3-Dihydroxy-2-propoxy)methyl]guanine (DHPG), illustrated below, has been approved by the U.S. Food and Drug Administration for use as an antiviral agent for human cytomegalovirus infections in AIDS patients.

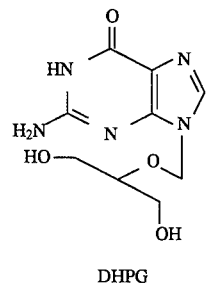

DHPG

Martin et al. and Ogilvie et al. have reported the synthesis of DHPG via the reaction of N-acetylguanine (Scheme 1) or 6-chloroguanine with 1,3-dibenzyloxy-2-chloromethoxypropane. J. C. Martin et al., 9-[(1,3-Dihydroxy-2-propoxy)methyl]guanine: A New Potent and Selective Antiherpes Agent. *J. Med. Chem.* 1983, 26(5), 759–761; K. K. Ogilvie et al. Biologically active acyclonucleoside analogues. II. The Synthesis of 9-[(2-hydroxy- 1-(hydroxymethyl)ethoxy]methyl]guanine (BIOLF-62), *Can. J. Chem.* 1982, 60, 3005–3010.

Scheme 1
Synthesis of DHPG According To The Method of
Martin et al. and Ogilvie et al.

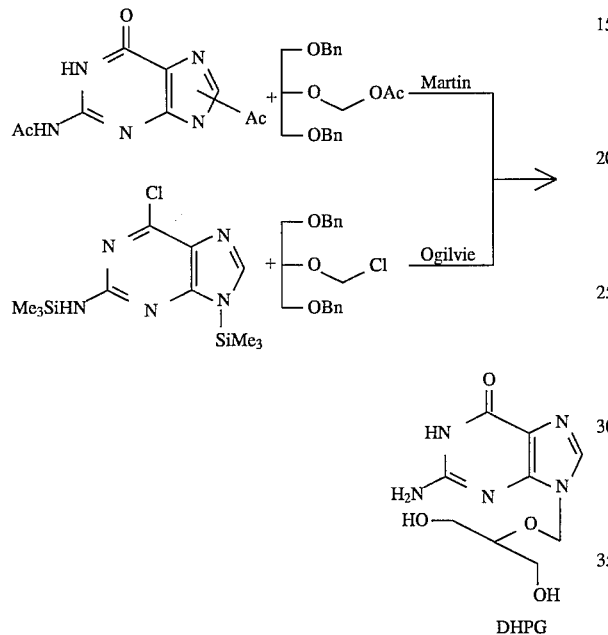

The reaction of N-acetylguanine and 1,3-dibenzyloxy-2-chloromethoxypropane in the presence of tributyl ammonium iodide provided a yield of 28% of the $N^7$-isomer and 28% of the $N^9$-isomer of the acetylated, dibenzylated product. It was also observed by the present inventors that, despite comments to the contrary in the article, the benzyl protected condensation intermediate produced in Scheme 1 was difficult to deprotect. Accordingly, it would be desirable to develop a procedure which does not require the use of this type of protecting group, and which provides a higher yield of the $N^9$-isomeric product.

6-Chloroguanine is not a preferred reagent for the industrial scale synthesis of DHPG because it is relatively expensive.

An alternative method for the production of DHPG was reported by A. K. Field et al. and W. I. Ashton et al. Field, A. K. et al., 9{[2-Hydroxyl-1-(hydroxymethyl)ethoxy]methyl}guanine: A selective inhibitor of herpes group virus replication. *Proc. Natl. Acad. Sci.*: USA, 1983, 80 4139–4143; Ashton, W. T. et al, European patent 0165164 A1, 1985. This procedure, illustrated in Scheme 2, involves the reaction of 1,3-diacetoxy-2-acetoxymethoxy propane with diacetylguanine and toluenesulfonic acid.

Scheme 2
Synthesis of DHPG Using the Method of Ashton and Field.

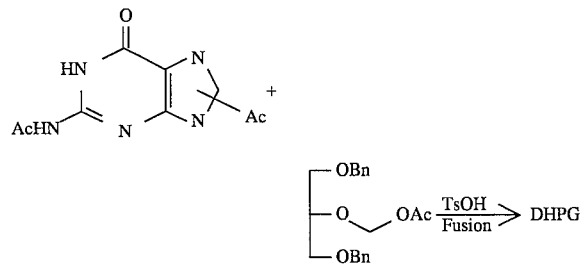

The key intermediate used in Scheme 2, namely, 2-acetoxymethoxy-1,3-diacetoxypropane, has been produced as illustrated in Scheme 3 (Field) or Scheme 4 (Ashton).

Scheme 3
Synthesis of 2-acetoxymethoxy-1,3-acetoxy propane from chloromethyl-1,3-dioxolane.

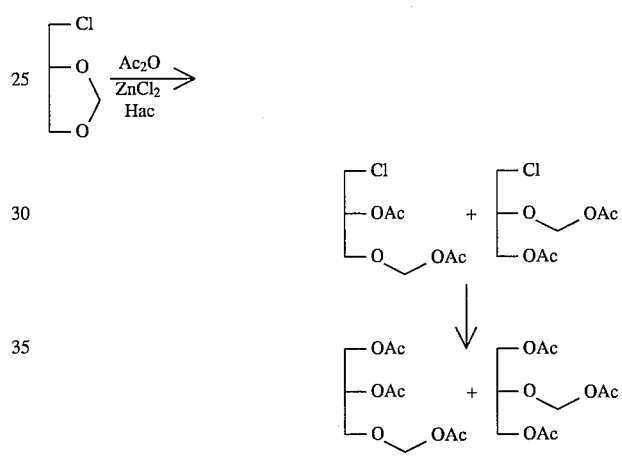

Scheme 4
Preparation of 2-acetoxymethoxy-1,3-acetoxy
propane from glycerol formal

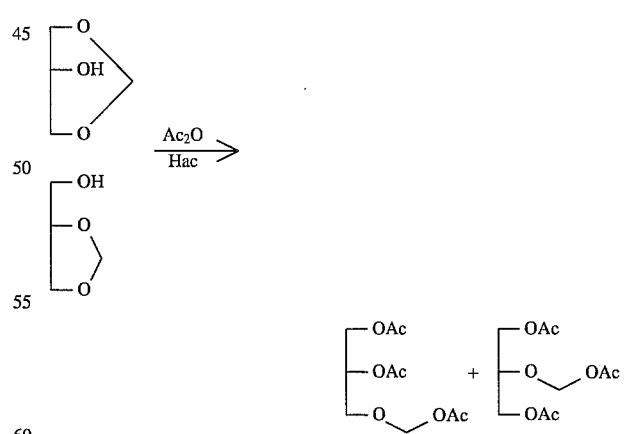

The syntheses shown in Schemes 3 and 4 are difficult to carry out, and they produce the desired product as a mixture of isomers which can only be separated with great difficulty using HPLC. This is not a commercially viable route for the production of these compounds.

Accordingly, it would be desirable to provide a method for the synthesis of acyclic guanine nucleosides, and in particular, acyclovir and DHPG, which can be carried out effectively on an industrial scale.

It is an object of the present invention to provide an improved method for the industrial production of acyclic purine nucleosides, and a particular, acyclic guanine nucleosides.

It is another object of the present invention to provide an improved method for the industrial preparation of acyclovir.

It is a further object of the present invention to provide an improved method for the industrial production of DHPG.

SUMMARY OF THE INVENTION

A method is provided for the preparation of acyclic guanine nucleosides that is suitable for industrial scale synthesis of the compounds. The method includes improved methods for the preparation of the starting materials, diacetylguanine, dioxolane diacetate (1-acetyl-2-acetylmethoxy-ethyleneglycol), and 2-acetoxymethoxy-1,3-acetoxy-propane (also referred to as 2-acetylmethoxy-1,3-acetylpropyleneglycol), improved methods for the alkylation of guanine, and improved isolation procedures. These methods are described in more detail below, with reference to the synthesis of the important compounds 9-(2-hydroxyethoxymethyl)-guanine (acyclovir) and 9-[(1,3-dihydroxy-2-propoxy)methyl]guanine ("DHPG"). Other acyclic guanine nucleosides can be prepared by standard modifications of the disclosed methods. All of these methods are considered to fall within the scope of the present invention.

In a broad embodiment, the invention is a method for the preparation of an acyclic guanine nucleoside comprising reacting $N^2,N^9$-diprotected guanine with an $N^9$-alkylating compound of the ROC(O)(lower alkyl), wherein R is an alkyl group of $C_1$ to $C_{10}$ that can include an oxygen as chain interrupting moiety and protected hydroxyl or amino groups, in the presence of acetic anhydride and a compound selected from the group consisting of phosphoric acid and polyphosphoric acid.

Acyclic guanine nucleosides other than acyclovir and DHPG prepared according to one or more of the methods disclosed herein can be used as antiviral agents or used in the evaluation of structure activity relationships of substrates with viral enzymes.

DETAILED DESCRIPTION OF THE INVENTION

I. Preparation of Acyclovir

Figure 1:
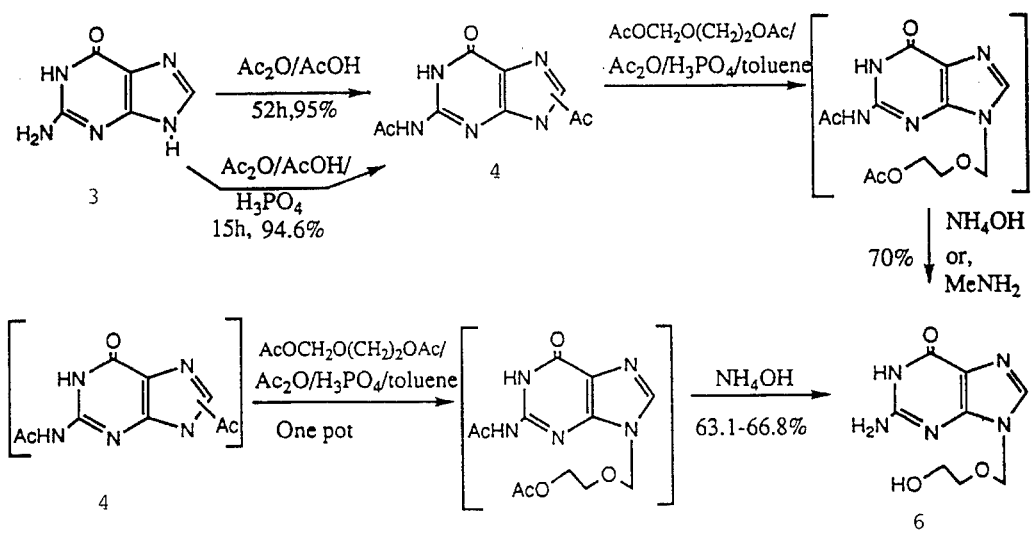
FIG. 1 shows one method for the synthesis of acyclovir according to the present invention.
Figure 2:
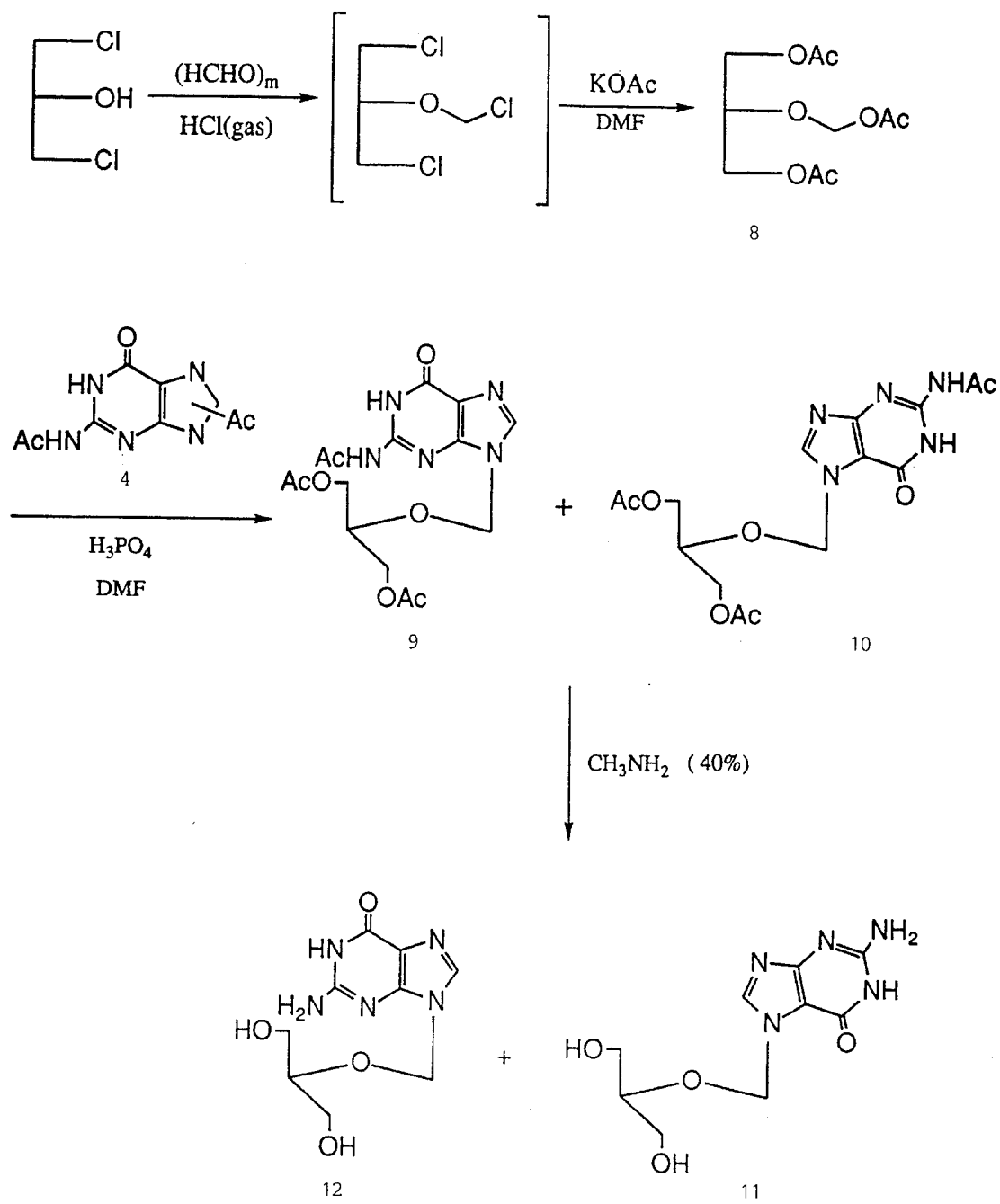
FIG. 2 shows one method for the synthesis of DHPG according to the present invention.

A method for the preparation of acyclovir is provided that is suitable for the commercial manufacture of the product. In a preferred embodiment of the first step, guanine is acetylated using acetic anhydride, acetic acid, and phosphoric acid. In a preferred embodiment of the second step, diacetyl guanine is alkylated at the $N^9$-position using $CH_3C(O)OCH_2O(CH_2)_2)OC(O)CH_3$, acetic anhydride and phosphoric acid or polyphosphoric acid. The acetyl groups are then removed as desired. Each of these steps is described in detail below.

1. Acetylation of Guanine

In the first step of the reaction, the 2-amino group of guanine is protected to prevent it from being alkylated in the second step of the reaction. In a preferred embodiment, the protecting group is acetyl. As mentioned in the Background of the Invention, a number of methods are available to acetylate guanine. Any of these methods can be used in the process described herein. Alternatively, other known methods to acetylate the 2-amino and $N^9$-position can be used.

In an alternative embodiment, other nitrogen protecting groups can be used, including but not limited to, for example, other lower alkyl carboxylic acids, benzoyl, p-nitrobenzoyl, toluyl, methylsulfonyl, or p-toluylsulfonyl. The choice of protecting group may effect the ultimate yield of product, in that protecting groups are removed with varying degrees of difficulty as known to those skilled in the art. The term lower alkyl, as used herein, refers to a saturated straight or branched hydrocarbon or a combination thereof, typically of $C_1$ to $C_6$, or a cyclic hydrocarbon for $C_3$, $C_5$ and $C_6$ and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

In general, in the process of protecting the 2-amino group, the $N^9$ group usually also reacts with the protecting group. Acylation, and in particular, acetylation, activates the $N^9$-position toward alkylation in the second step, and therefore, is desirable.

In a preferred reaction scheme, a combination of an acid and anhydride are used. In general, it is preferred to use a symmetrical anhydride in the reaction scheme that corresponds to the acid used. For example, acetic acid is preferably used in combination with acetic anhydride, and propionic acid is preferably used in combination with propionic anhydride.

The acylation reaction can be carried out at any temperature that provides the desired results. A convenient temperature range is between 50 and 200 degrees Celsius, and more narrowly, between 80 and 140 degrees Celsius.

The acylation reaction is allowed to proceed as long as necessary to obtain the desired product in a desired purity. In general, it has been found that a reaction time of between 30 minutes and five hours, and more narrowly, between 30 minutes and three hours, is typically appropriate. A method to acetylate guanine is illustrated in detail in the following working example. Given the present disclosure, one of ordinary skill in the art can routinely modify the process as necessary. All of these modifications are considered to fall within the scope of the present invention.

Example 1

Preparation of Diacetylguanine (4)

In an attempt to identify suitable conditions for the industrial preparation of diacetylguanine, the reaction conditions under which the acetylation occurs were evaluated. First, Matsumoto's procedure for the preparation of diacetyl guanine was modified by the substitution of sulfuric acid and phosphoric acid for the acid catalysts evaluated by Matsumoto. It was determined that the use of sulfuric acid resulted in colored product, and was therefore not an acceptable acid for industrial scale acetylation of guanine. It was discovered that phosphoric acid, however, did not cause discoloration of the product and provided a useful yield of product.

The effect of the ratio of acetic anhydride and acetic acid on the reaction time and yield was also studied. In general, any range of acetic anhydride, acetic acid, guanine and phosphoric acid can be used that provides the desired results. In the present work, it was found that a ratio of 15/10/1/0.05 (ml) of $Ac_2O$/AcOH/guanine/$H_3PO_4$ is preferred. It was discovered that guanine could be acetylated using this ratio of reactants at reflux for 15 hours to give diacetylguanine with minimal discoloration in approximately 94% yield.

Two methods for the preparation of diacetylguanine 4 (FIG. 1) were explored. Both provided compound 4 in excellent yields.

(a) A mixture of guanine 3 (100 g, 0.662 mol), acetic anhydride (1000 ml, 10.59 mol) and acetic acid (1500 ml, 26.25 mol) was refluxed for 52 hours, during which time the reaction mixture became an almost clear solution. Excess acetic anhydride and acetic acid were then removed by distillation. The residue (solid and liquid) was cooled to 0° C. The resulting solid was collected by filtration, washed twice with water (100 ml), twice with methanol (50 ml), and then dried at 60° C. in vacuo. The yield of 4 was 144.97 g (93.2%), mp. 260° C. UV λmax (50% v/v MeOH—$H_2O$) 215.5, 254.5, 292; (0.1M HCl) 211,258; (0.1M NaOH) 227,268.5 nm. $^1$H-NMR(DMSO-$d_6$): δ 2.2(s, 3H, Ac), 2.8(s, 3H, Ac), 8.44(s 1H, H-8), 11.95 (br, 2H, NH,NH,$D_2O$ exchangeable).

The filtrate (water and methanol) from the above procedure was concentrated to near dryness and cooled to 0° C. The resulting solid was collected by filtration, washed three times with water (10 ml), three times with methanol (10 ml), and then dried. The yield of additional 4 was 4.265 g (2.76%). The total yield of 4 was 149.265 g (95.9%).

(b) A mixture of guanine 3 (30 g, 0.199 mol), acetic anhydride (450 ml), and acetic acid (300 ml) was heated to reflux. Phosphoric acid (85.5%, 1.5 ml) was added to the mixture and the mixture then refluxed for 15 hours. Some product precipitated on the side of flask. Solvents were removed under reduced pressure (water aspirator) to dryness. After cooling, the resulting solid was collected, and then washed twice with water (30 ml) and methanol (20 ml) to give diacetylguanine (42.5 g, 91%). The filtrate (water and methanol) obtained above was concentrated to near dryness to give additional 4 (1.7 g, 3.6%). The total yield of 4 was 44.26 g (94.6%).

2. Preparation of Dioxolane-diacetate (2)

The preferred starting material, 1,3-dioxolane diacetate (1-acetyl-2-acetylmethoxy-ethyleneglycol), can be prepared using any method known to those skilled in the art. In an alternative embodiment, a starting material of the formula R"OCH$_2$O(CH$_2$)$_2$OR' can be used in the process, wherein R' and R" are oxygen protecting groups, and preferably acyl groups. The term oxygen protecting group refers to a moiety that is added to oxygen to prevent its further reaction during the course of derivatization of other moieties in the molecule. A wide variety of oxygen protecting groups are known to those skilled in the art of organic synthesis, for example, as taught in Greene, et al., "Protective Groups in Organic Synthesis," John Wiley and Sons, Second Edition, 1991.

In one embodiment, the dioxolane ring is opened using acetic anhydride as the ring-opening reagent in the presence of catalytic amounts of p-toluenesulfonic acid. This provided dioxolane-diacetate in 80% yield after distillation by the method disclosed in Chen et al. *J. China Pharm. Univ.* 1992, 23(1), 43.

A process for the production of dioxolane-diacetate 2 is set forth below in Scheme 5.

Scheme 5
Preparation of Dioxolane-diacetate.

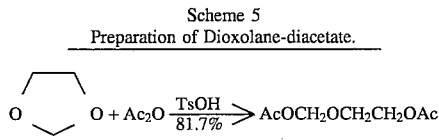

Example 2

Preparation of Dioxolane-diacetate

Dioxolane 1 (224 g, 99%, 211.6 ml, 3 mol) was added dropwise to a solution of p-toluenesulfonic acid monohydrate (10 g, 0.053 mol) in acetic anhydride (306 g, 283.3 ml,3 mol) and acetic acid (45 g, 42.9 ml, 0.75 mol) precooled to below 10° C. at the rate that maintained the reaction temperature under 30° C. The solution was then stirred for an additional hour at a temperature under 30° C., and then distilled. The first portion of distillate was collected at a temperature of 35°–80° at 1.5 mm Hg and contained acetic acid, acetic anhydride, and other materials. The second portion of distillate was collected at 80°–95° C. at 0.75 mm Hg. The second portion was redistilled to give pure 2 in a yield of 431.5 g (81.7%, bp. 78°–84° C. at 0.5 mm Hg).

3. Alkylation of Diacetylguanine

In the next step of the synthesis, the diacetylated (or otherwise protected) guanine from step 1 is alkylated in the $N^9$-position to produce 2-acetamido-9-(2-acetylethoxymethyl)guanine.

One method for the preparation of acyclovir according to the present invention is illustrated in FIG. 1 and described in detail in Example 3. Standard variations and modifications of this method are considered to fall within the scope of the invention.

The conditions under which diacetylguanine is alkylated was studied in detail to design the appropriate industrial scale preparation of acyclovir, including $N^9$/$N^7$-isomerization, acid catalyst used, reaction temperature, reaction time, amount of dioxolane diacetate used, and amount of solvent used. These evaluations are described in detail following Example 3.

As described in detail in Example 4, acyclovir or other acyclic guanine nucleosides can be prepared in a one-pot procedure if desired.

Example 3

Preparation of Acyclovir (6) (Toluene Procedure)

Two methods were used to prepare acyclovir 6 from the reaction of diacetyl guanine 4 with dioxolane diacetate 2.

(a) Phosphoric acid (85.5%, 1.5 ml) was added to a mixture of 2 (75 g, 426 mmol), 4 (50 g, 213 mmol) and acetic anhydride (5 g) in toluene (300 ml) with stirring. The resulting mixture was refluxed for 24 hours with vigorous stirring. After refluxing, toluene and acetic anhydride were removed under reduced pressure (water aspirator). The residue was then heated at 120°–130° C. (oil bath) under reduced pressure (100 mm Hg) for another two hours, cooled to room temperature, and triturated with toluene (250 ml) while stirring overnight. The resulting solid was collected by filtration, dissolved in ammonium hydroxide (30%, 300 ml), and stirred at room temperature for 24 hours.

The resulting mixture was concentrated to dryness under reduced pressure (water aspirator). The solid residue was triturated with methanol (150 ml). The resulting mixture was heated at 80° C. for one hour and allowed to remain at room temperature overnight. The resulting solid was collected by filtration and then recrystallized from water (1500 ml). It was cooled to room temperature, and then stored in the refrigerator overnight. The resulting solid was collected by filtration, washed twice with methanol (20 ml), and dried in vacuo to give pure acyclovir (34.06 g, 71.1%), mp. 244°–246° C. UV λmax (50% v/v MeOH—$H_2O$) 206, 252, 268 (sh); (0.1M HCl) 209.5, 255.5, 270 (sh); (0.1m NaOH) 219.5, 265 nm; $^1$H-NMR (DMSO-d6): δ 3.45, 3.48 (d, 4H, $CH_2CH_2$), 4.64 (br, 1H, OH $D_2O$ exchangeable), 5.34 (s, 2H, $OCH_2O$), 6.47 (s 2H, $NH_2D_2O$ exchangeable), 7.80 (s, 1H, 8-H), 10.60 (s, 1H, NH $D_2O$ exchangeable). The mother liquor (aqueous solution) was concentrated to give a second crop of a solid material (4.7 g) which contained the $N^7$-isomer of 6. The ratio of $N^9$:$N^7$ isomers in the second crop was 1:6.6. The second crop also contained some acetamide (by $^1$H NMR).

(b) (Methylamine method). Phosphoric acid (85.5%, 1.5 ml) was added to a mixture of 2 (75 g, 426 mmol), 4 (50 g, 213 mmol) and acetic anhydride (5 g) in toluene (300 ml) with stirring. The resulting mixture was refluxed for 24 hours with vigorous stirring. After refluxing, toluene and acetic anhydride were removed under reduced pressure (water aspirator). The residue was then heated at 120°–130° C. (oil bath) under reduced pressure (100 mm Hg) for another 2 hours, cooled to room temperature, triturated with ethyl acetate (100 ml) and stirred overnight. The resulting solid was collected by filtration, dissolved in methylamine (40%, 300 ml), and refluxed for one hour. The resulting mixture was concentrated to dryness under reduced pressure (water aspirator). The residue (solid) was triturated with methanol (100 ml). The resulting mixture was stored in the refrigerator for 5 hours. The resulting solid was collected by filtration and then recrystallized from water (1600 ml) and activated carbon (1 g). After recrystallization, the solid was cooled to room temperature and then stored in the refrigerator overnight. The resulting solid was collected by filtration, washed twice with methanol (20 ml), and dried in vacuo to give pure acyclovir 6 (34.29 g, 71.6%).

The mother liquor (aqueous solution) was concentrated to provide a second crop of a solid material (2.5 g) which contained the $N^7$-isomer of 6 in a ratio of $N^9$:$N^7$ of 1:22.3). The second crop of crystals also contained acetamide (by $^1$H NMR).

Example 4

Preparation of Acyclovir from Guanine (One-pot Procedure)

A mixture of guanine 3 (32.13 g, 213 mmol), acetic anhydride (320 ml) and acetic acid (480 ml) was refluxed for 52 hours, during which time the mixture became an almost clear solution. The liquid was removed by distillation to dryness. To the residue (solid) was added toluene (300 ml), 2 (75 g, 426 mmol), and phosphoric acid (85.5%, 1.5 ml) with stirring. The resulting mixture was refluxed for 24 hours with vigorous stirring.

Toluene and acetic anhydride were then removed under reduced pressure (water aspirator) and the residue was heated at 120°–140° C. (oil bath) under reduced pressure (100 mm Hg) for another 2 hours, cooled to room temperature, triturated with ethyl acetate (100 ml), and stirred at room temperature overnight.

The resulting solid was collected by filtration, washed twice with ethyl acetate (25 ml), dissolved in ammonium hydroxide (30%, 300 ml), and stirred at room temperature for 24 hours. This mixture was concentrated to dryness under reduced pressure (water aspirator). The residue was treated with methanol (150 ml) and the resulting mixture was heated at 80° C. for 1 hour, cooled, and allowed to stand at room temperature overnight. The resulting solid was collected by filtration and recrystallized from water (1700 ml) using 1 gram of activated carbon. The filtrate was cooled to room temperature, and stored in the refrigerator overnight. The resulting solid was collected by filtration, washed twice with methanol (20 ml), and dried to give pure acyclovir 6 (30.2–31.97 g, 63.1–66.8%). The mother liquor was concentrated to give second crop (2.43–2.765 g) which contained the $N^7$-isomer (below 5%) and acetamide (by $^1$H NMR).

Minimization of $N^9$/$N^7$-Isomeric Mixtures

To achieve a high efficiency of reaction for industrial scale synthesis of acyclovir, it is necessary to minimize or eliminate alkylation of the $N^7$-position. As discussed in the Background of the Invention, Chen et al., *J. China Pharm. Univ.* 1992, 23(1), 43, reported the preparation of acyclovir by the reaction of diacetylguanine with dioxolane in the presence of p-toluenesulfonic acid. The product was a syrup containing a mixture of $N^9$/$N^7$-isomers in which the ratio of $N^9$/$N^7$-isomers was about 3/2 in favor of the $N^9$-isomer. Contrary to the article, however, the present inventors did not observe any significant amount of $N^9$-isomer precipitating from this syrup after treatment with chloroform.

On monitoring this reaction by thin layer chromatography, it was determined that the condensation of diacetyl guanine with dioxolane-diacetate in the presence of acidic catalyst produced $N^7$-isomer first, which was partially converted to $N^9$-isomer to reach an equilibrium in the ratio of 3/2 in favor of $N^9$-isomer. Under these condensation conditions, pure $N^7$- or $N^9$-acyclovir diacetate could be converted to give the same equilibrated mixture. This observation resulted in one of the embodiments of the improved process for the production of acyclovir of the present invention. When diacetyl guanine (4) almost disappeared during the condensation reaction, the reaction mixture was concentrated to dryness in vacuo, during which time the ratio of $N^9$/$N^7$-isomer continuously changed from approximately 3/2 to nearly one spot ($N^9$-isomer) as indicated by thin layer chromatography. The pure acyclovir diacetate (5) was obtained by simply washing with chloroform in good yield. It was surprising to learn that the ratio of $N^9$/$N^7$-isomers could be significantly manipulated in this manner.

Therefore, in one embodiment of the invention, a method is provided for the preparation of acyclovir diacetate by the condensation of diacetylguanine (or otherwise protected guanine) with dioxolane-diacetate (or its equivalent) in the presence of an acidic catalyst, followed by heating the reaction mixture, optionally in vacuo, at a point in time when diacetylguanine has disappeared or almost disappeared from the reaction mixture. The mixture can be heated to any temperature that causes isomerization of the $N^7$-isomer to the $N^9$-isomer. A typical temperature range is between 50 and 180 degrees Celsius, and a preferred range is between 100 and 120 degrees Celsius.

While this process represents a surprising improvement in the process for the production of acyclovir, the yield may vary due to the polymerization of dioxolane-diacetate 2 under the reaction conditions, resulting a sticky material which is difficult to handle, if a proper solvent is not selected. A good yield of acyclovir diacetate is observed with the use of recovered dioxolane diacetate as a condensing reagent, which presumably contains some ethylene glycol-diacetate generated from the decomposition of 2. The condensation of 4 with two equivalents of 2 in ethylene glycol-diacetate in the presence of catalytic amounts of phosphoric acid, gave pure 5 in 80–85% yield. Aromatic and alkylaromatic solvents are also useful in this regard. This is discussed in more detail below, in the section on the effect of solvent on the reaction.

Effect of Acid Used

The effect of acid catalyst on the alkylation reaction was also studied. A variety of acids were evaluated using ethylene-glycol diacetate as the solvent. The catalysts which were examined included p-toluenesulfonic acid, sulfanilic acid, 2,4-dinitrobenzoic acid, p-nitrobenzoic acid, sulfuric acid, phosphoric acid and polyphosphoric acid. The results are provided in Table 1.

As indicated in Table 1, phosphoric and polyphosphoric acid provided the best product and yields. The yields of acyclovir 6 produced via the condensation reaction of diacetylguanine 4 using phosphoric acid and polyphosphoric acid as the catalyst were 71.1% and 72.6% respectively.

p-Toluenesulfonic acid, sulfuric acid, and sulfanilic acid were also good catalysts. However, the condensation reaction, which was carried out in ethylene glycol-diacetate, became a almost clear solution and it was difficult to crystallize the $N^9$-alkylated product from this solution. In contrast, the $N^9$-alkylated product was isolated easily from the phosphoric acid- or polyphosphoric acid-containing solution.

used, the condensation reaction did not proceed to completion. Thus, two equivalents of 2 seemed to give the best results under these reaction conditions.

Therefore, it appears that while any ratio of dioxolane diacetate can be used that achieves the desired results, a ratio of between 1.5 and 3 equivalents of the diacetate to guanine base is preferred.

Effect of Solvent

The condensation reaction was carried out under the conditions described in Example 3 using toluene, dimethyl formamide (DMF), dioxane, and ethylene glycol-diacetate. The results are provided in Table 2.

While ethylene glycol diacetate is a good solvent for the condensation reaction, it may not be as appropriate for an industrial preparation of 6 as other organic solvents, in view of its high boiling point (186°–187° C.).

Toluene appears to be the best solvent, as it allowed the easy crystallization of 5 from the reaction mixture, and has a suitable boiling point for industrial use. Alternatively suitable solvents include xylene, cumene, benzene, and other aromatic-based solvents, especially alkylated aromatic solvents.

After removing the acetyl groups, the yield of pure 6 using toluene was 70%. When the condensation was conducted in DMF or dioxane, the product still contained a small amount of $N^7$-isomer (ca 3%) after recrystallization from water and the yield was lower.

TABLE 1

Effect of catalysts on the yield of acyclovir (6)

| | Condensation condition | | | |
|---|---|---|---|---|
| Catalyst | Reaction temperature | Reaction time (hours) | solvent | Yield of 6 (%) |
| polyphosphoric acid | 120–125° C. | 1.5 | ethylene- | 72.6 |
| phosphoric acid | 120–125° C. | 1.5 | glycol- | 70.7 |
| p-toluenesulfonic acid | 120–125° C. | 1.5 | diacetate | 63.8 |
| sulfanilic acid | 120–125° C. | 2.8 | same | 64.2 |
| sulfuric acid | 120–125° C. | 6 | same | 53.3 |
| p-nitrobenzoic acid | 120–125° C. | very slow* | same | ND |
| 2,4-dinitrobenzoic acid | 120–125° C. | very slow* | same | ND | note:
Deacetylation was accomplished in ammonium hydroxide;
*indicated more than 48 h.

Effect of the Amount of Dioxolane-diacetate Used (2)

The amount of dioxolane-diacetate 2 used in the condensation reaction set forth in Example 3 also affected the yield of acyclovir 6. When different amounts of 2 (3 equivalents and 2 equivalents) were used in condensation, the yield of 6, after removal of the acetyl groups, was 57% and 70%, respectively.

One explanation of the lower yield in the presence of a greater amount of 2 is that 2 may polymerize when large excesses are present. This results in the lower $N^9/N^7$ ratio at the end of the reaction. When 1.5 of equivalents of 2 was

TABLE 2

Effects of solvent on the yield of acyclovir (6)

| Solvent | Reaction temperature | Reaction time (hours) | Yield of 6 |
|---|---|---|---|
| toluene | reflux | 24 | 71.1% |
| ethylene glycol-diacetate | 120–125° C. | 2 | 70% |

TABLE 2-continued

Effects of solvent on the yield of acyclovir (6)

| Solvent | Reaction temperature | Reaction time (hours) | Yield of 6 |
|---|---|---|---|
| DMF | 120–125° C. | 1 | 65.3% |
| dioxane | reflux | 5 | 56.2% |

Effect of Reaction Temperature and Time

The condensation reaction set forth in Example 3 was monitored by thin layer chromatography ("TLC") to determine the effect of temperature on the condensation. This evaluation indicated that the condensation reaction was slow at temperatures under 110° C. and that the side reaction was pronounced at temperatures higher than 140° C. The best yield of 5 was obtained at temperatures between 110°–130° C., and optimally, between 110 and 120 degrees Celsius. If the reaction mixture was heated for a long time (more than 48 hours), the reaction mixture became brown and more side products appeared to be formed.

Recyclizing the Mixture of Acyclovir and Its $N^7$-isomer a) Differential Solubility The solubility of the mixture of 6 and its $N^7$-isomer was examined in different solvents, including methanol, ethanol, isopropanol, ethyl acetate, acetonitrile, DMF, and water.

The mixture did not dissolve in acetonitrile or isopropanol. Triturating the mixture with methanol or ethanol did not significantly change the ratio of $N^9$- and $N^7$-acyclovir in the filter cake from that of the initial mixture.

Triturating the mixture with water, however, proved to be useful. The content of the $N^7$-isomer in water solution was much more than that in either the filter cake or the starting mixture. Therefore, water may be used as a solvent for recrystallization of 6 containing a small amounts of its $N^7$-isomer. In addition, acyclovir 6 completely dissolves in DMF while the $N^7$-isomer does not dissolve in DMF. Accordingly, these two compounds can easily be separated by triturating with DMF.

b) Chemical Conversion

The mixture which contained the $N^9$- and $N^7$-isomer of 6 was acetylated with 3 equivalents of $Ac_2O$ in the condensation condition to give an equilibrated mixture of 5 and its N-isomer. If 15% of the above mixture was added to the original condensation mixture, which normally gives approximately a 70% yield, 6 was obtained in 72.3% yield from 4 and the added mixture (15% of the above mixture) after workup followed by deblocking the acetyl groups.

Example 4

Preparation of Acyclovir (6) from Diacetylguanine (4) Including Recycling of a Mixture of Acyclovir and $N^7$-isomer Phosphoric acid (85.5%, 1.5 ml) was added to a mixture of 2 (75 g, 426 mmol), (50 g, 213 mmol), acetic anhydride (5 g), and toluene (300 ml) with stirring. The resulting mixture was refluxed for 20 hours with vigorous stirring. At that time, a mixture of acyclovir 6 and its $N^7$-isomer (7.5 g, 33.3 mmol, the ratio of $N^9/N^7$ 20/1) was added to the reaction mixture. The resulting mixture was stirred at reflux for another 5 hours. Toluene and acetic anhydride were then removed under reduced pressure (water aspirator). The residue was heated at 120°–130° C. (oil bath) under reduced pressure (100 mm Hg) for another 2.5 hours, cooled to room temperature, treated with toluene (250 ml), and stirred at room temperature overnight. The resulting solid was collected by filtration, washed with toluene (50 ml), dissolved in ammonium hydroxide (30%, 400 ml) and stirred at room temperature for 24 hours. This mixture was concentrated to dryness under reduced pressure (water aspirator). The residue was treated with methanol (200 ml). The resulting mixture was heated at 80° C. for 1 hour and allowed to stay at room temperature overnight. The resulting solid was collected by filtration and recrystallized from water (1800 ml). After cooling to room temperature and storage in the refrigerator overnight, the resulting white solid was collected by filtration, washed twice with methanol (20 ml), and dried to give pure acyclovir 6 (40.015 g, 72.3%).

The mother liquor (water) was concentrated to give the second crop of solid material (6.6 g) containing $N^7$-isomer in a ratio of $N^9:N^7$ of 1:3.5). The second crop of solid material also contained acetamide (by $^1H$ NMR).

Example 5

Separation of Acyclovir from a Mixture of Acyclovir and Its $N^7$-isomer

Acyclovir 6 (5 g) which contained a mixture of approximately 5% of the $N^7$-isomer was dissolved in DMF (125 ml) and stirred at room temperature overnight. The mixture was filtered to obtain a cake (0.573 g, 11.5%) which contained 6 (13.5%) and the $N^7$-isomer (86.4%) according to the $^1$H-NMR spectrum. The filtrate was concentrated to dryness. The residue (solid) containing the $N^7$-isomer (1.2%) was recrystallized from water (150 ml) to give acyclovir (3.84 g, 76.8%).

Deacetylation of Acyclovir Diacetate

Acyclovir diacetate can be deacetylated using any method and with any reagents for this purpose known to those of skill in the art. Nonlimiting examples of reagents include, but are not limited to, any suitable base, such as ammonium hydroxide, methylamine, potassium hydroxide, or sodium hydroxide.

Ammonium hydroxide or methylamine were used as the deacetylating agent to remove the acetyl groups from compound 5. Both methylamine and ammonium hydroxide proved to be good deacetylating agents. Although the workup is easier using methylamine than it is using ammonium hydroxide, on an industrial scale, the smell of methylamine may dictate the preferred use of ammonium hydroxide as a the deacetylation agent.

II. Preparation of DHPG

In a second embodiment of this invention, 9-[(1,3-dihydroxy-2-propoxy)methyl]guanine is prepared using an improved route for the preparation of the key intermediate 2-acetoxymethoxy-1,3-diacetoxypropane 8 and improved procedures for the condensation of 2-acetoxymethoxy-1,3-diacetoxypropane with guanine.

1. Preparation of 2-Acetoxymethoxy-1,3-Diacetoxypropane

As discussed in the Background of the Invention, the methods of Field and Ashton for the preparation of 2-acetoxymethoxy-1,3-diacetoxypropane are not preferred because they lead to the preparation of two compounds (see Schemes 3 and 4) that must be separated by HPLC or other means.

An improved process for the preparation of key intermediate 2-acetoxymethoxy-1,3-diacetoxypropane 8 is provided that results in the formation exclusively of the desired product, as illustrated in Scheme 6.

Scheme 6
Preparation of 2-Acetoxymethoxy-1,3-diacetoxypropane (8)

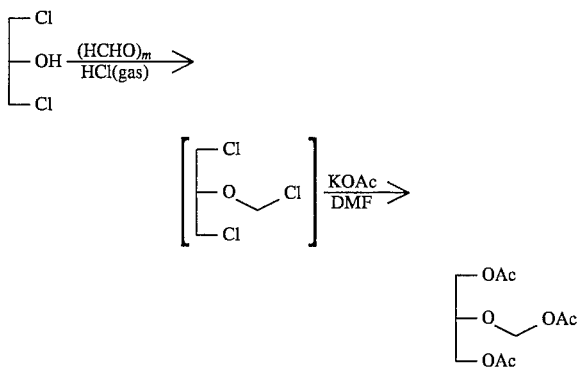

The method involves the reaction of 1,2-dichloro-2-propanol, hydrogen chloride and paraformaldehyde. Hydrogen bromide or hydrogen iodide can be used in place of hydrogen chloride. The reaction is preferably carried out under dry conditions, using excess HCl, paraformaldehyde, and KOAc. In place of KOAc, NaOAc or LiOAc can be used. Suitable solvents for the reaction include DMF, DMSO, benzene, and toluene. The reaction of hydrogen chloride, 1,2-dichloro-2-propanol, and paraformaldehyde is carried out at any suitable temperature, typically between −30 and 25 degrees Celsius. The reaction of acetate base with the product of reaction of hydrogen chloride, 1,2-dichloro-2-propanol, and paraformaldehyde is also carried out at any suitable temperature, and typically between 50 and 200 degrees Celsius.

The reaction is described in detail in Example 6. Modifications of this reaction are considered to fall within the scope of this invention.

Example 6

Preparation of
2-Acetoxymethoxy-1,3-diacetoxypropane 8

Hydrogen chloride was bubbled into a mixture of 1,2-dichloro-2-propanol (200 g, 155 mol) and paraformaldehyde (93 g, 3.1 mol) in dry $CH_2Cl_2$ (3600 ml). The mixture was cooled in an ice-bath for 4 hours with mechanical stirring. The mixture became nearly homogeneous, and was stirred for another 1.5 hours. The reaction solution was then dried over anhydrous $MgSO_4$ overnight.

The $CH_2Cl_2$ solution was evaporated under reduced pressure to give 360 g of colorless liquid, which was mixed with potassium acetate (760 g, 7.75 mol) in dry DMF (2800 ml), stirred at room temperature for 19 hours, and then heated at 120°–125° C. (oil bath) for 10 hours.

After filtration to remove the salt, the filtrate was evaporated under reduced pressure to remove the solvent. The residue was dissolved in 2000 ml of ethyl acetate, washed with a saturated NaCl solution (500 ml) and washed four times with water (500 ml) and then dried over anhydrous $MgSO_4$. The ethyl acetate solution was refluxed with charcoal for 30 min. and filtered on Celite pad. The filtrate was evaporated in vacuo to give a brown syrup (280 g).

The brown syrup was passed through a short vacuum silica gel column to eliminate impurities using ether/petroleum ether (10–12%) to give a light-yellow liquid, which was distilled at 140°–141°/0.75 mm Hg to give a colorless liquid (144 g, 37.5%). $^1H$ NMR (DMSO-$d_6$) δ 5.26 (s, 2H, $OCH_2O$), 4.04–4.15(m, 5H, $CH(OCH_2)_2$), 2.05 (s, 3H, AcN), 2.03 (s, 6H, AcO).

2. Condensation of Diacetylguanine with Acetoxymethoxy-1,3-diacetoxypropane

Field, et al., and Ashton, et al., have reported the condensation of diacetylguanine with acetoxymethoxy-1,3-diacetoxypropane at 155–160 degrees Centigrade in fusion using toluenesulfonic acid as a catalyst.

In one embodiment of the present invention, the condensation is carried out at a temperature of approximately 120° C. or less in a solution of DMF or other suitable solvent using phosphoric acid or polyphosphoric acid as the catalyst. This minimizes the formation of side-products and provides a superior yield to that reported by prior methods. The process produces the condensation product in yields of 32.6–40.4%. In contrast, the reported yields in Field et al., and Ashton et al. were 14–31%.

Due to the formation of the $N^7$- and $N^9$-isomers 9 and 10 during the condensation, which have similar properties, other reported methods (Field et al. and Ashton et al. as well as Martin et al. and Ogilvie et al.) required the use of column chromatography or other procedures to separate the two isomers, which can be a laborious and time-consuming process.

The disclosed method avoids the use of column chromatography by selective crystallization of the reaction products. The mixture of 9 and 10 was obtained as a solid by precipitation from ethylene glycol dimethyl ether solution of condensation product syrup. The mixture was deblocked without separation, followed by trituration with DMF. Evaporation of DMF solution mainly containing 12, followed by decolorization and recrystallization, gave the final product 12. Column chromatography was used only to separate the mother liquor after ethylene glycol dimethyl ether treatment.

Example 7

Preparation of
9-{[2-Acetoxy-1-(acetoxymethyl)ethoxy]methyl}-2-acetamidopurine-6-one (9) and
7-{[2-acetoxy-1-(acetoxymethyl)ethoxy]methyl}-2-acetaminopurine-6-one (10)

A mixture of diacetylguanine (10.575 g, 45 mmol), 2-acetoxymethoxy-1,3-diacetoxypropane (22.32 g, 90 mmol) and phosphoric acid (0.3 ml) in DMF (45 ml) was heated for three hours at 120° (oil bath 135°) with stirring. The suspension gradually became homogeneous. When TLC indicated the reaction was complete, the reaction solution was evaporated in vacuo to remove solvents yielding a dark-brown syrup.

The syrup was dissolved in small amount of $CHCl_3$ and applied to a column (silica gel 60, φ4×27 cm), eluted with $CH_3OH:CHCl_3$ (0–3%) to give 9 (8.0 g, 46.7%) and 10 (5.1 g, 29.8%).

Compound 9: mp 165°–7° (ethyl acetate); $R_f$ 0.49 ($CH_3OH$—$CHCl_3$=1:9); UV ($CH_3OH$) $\lambda_{max}$ 254.5, 278.0 (sh); $^1H$ NMR (DMSO-$d_6$) δ 12.07, 11.78 (NH, s, 2H, $D_2O$ exchangeable), 8.14 (s, H, 8-H), 5.53 (s, 2H, $OCH_2N$), 4.11–3.94 (m, 5H, $(OCH_2CH)_2CH$), 2.18 (s, 3H, AcN), 1.88 (s, 6H, AcO).

Compound 10: mp 176°–178°; $R_f$ 0.61 ($CH_3OH$:$CHCl_3$=1:9); UV ($CH_3OH$) $\lambda_{max}$ 261.5 nm; $^1H$ NMR (DMSO-$d_6$) δ 12.18, 11.63 (s, 2H, NH, $D_2O$ exchangeable), 8.38 (s, 1H, 8-H), 5.73 (s, 2H, $OCH_2N$), 4.14–3.92 (m, 5H, $(OCH_2CH)_2CH$), 2.17 (s, 3H, AcN), 1.88 (s, 6H, AcO).

Example 8

Preparation of 9-(1,3-dihydroxy-2-propoxymethyl)guanine 12 and 7-(1,3-dihydroxy-2-propoxymethyl)guanine 11

Compound 9 (8.0 g) was dissolved in 100 ml of aqueous methylamine (40%) and gently refluxed for 1.5 hours, and then was evaporated to dryness to give a white solid. The solid was crystallized from 50 ml of water and 10 drops of acetic acid (to neutralize amine and remove the color) to give a white crystalline product 12 (4.63 g, 87%). mp>300° (dec.); $R_f$ 0.62 ($CH_3OH$:$CHCl_3$=1:1); UV ($H_2O$) pH7 $\lambda_{max}$ 251.5 (ε 10180), 272.0 (sh, ε 7500), pH2 $\lambda_{max}$ 253.5 (ε9840), pH 11 $\lambda_{max}$ 265.6 (ε 8060); $^1H$ NMR (DMSO-$d_6$) δ 10.64 (s, 1H, AcNH, $D_2O$ exchangeable), 7.80 (s, 1H, 8-H), 6.49 (s, 2H, $NH_2$ $D_2O$ exchangeable), 5.43 (s, 2H, 1'-H), 4.61 (t, 2H, OH, $D_2O$ exchangeable), 3.55–3.28 (m, 5H, 4'-H, 5'-H, 3'-H).

Compound 10 (1 g) was reacted as described above in 8 ml of aqueous methylamine (40%) to give a white crystalline product 11 (0.637 g, 95%). mp >=300° (dec); $R_f$ 0.62 ($CH_3OH$:$CHCl_3$=1:1); UV ($CH_3OH$), $\lambda_{max}$ 286.5, 244.5; $^1H$ NMR (DMSO-$d_6$) δ 10.87, (s, 1H, AcNH, $D_2O$ exchangeable), 8.09 (s, 1H, 8-H), 6.21 (s, 2H $NH_2$ $D_2O$ exchangeable, 5.65 (s, 2H, 1'-H), 4.59 (t, 2H, OH, $D_2O$ exchangeable), 3.60–3.24 (m, 5H, 3'-H, 4'-H, 5'-H).

Example 9

Isomerization of $N^7$ DHPG to $N^9$ DHPG

Compound 10 (2 g, 5.25 mmol) was dissolved in DMF (5 ml) and heated for three hours at 120° with stirring. TLC indicated no change in the reaction mixture. After three hours, 2-acetoxy-methoxy-1,3-diacetoxypropane 8 (3.906 g, 15.75 mmol) and $H_3PO_4$ (0.3 ml) were added to the solution, and the mixture was heated at 120° for 15 hours with stirring. TLC showed the formation of $N^9$ product and that the approximate ratio of $N^7$:$N^9$ was 1:1. The reaction solution was evaporated to dryness and treated with aqueous methylamine (40%, 50 ml) at gentle refluxing for 1.5 hours and then evaporated to give a yellow solid, which was triturated with DMF (40 ml). After filtration, the filtrate was evaporated to dryness and residue was crystallized from water to give a light-yellow solid product (0.343 g, 25.7% based on 10) which was identified as DHPG.

Example 10

Preparation of DHPG (12)

Another method for the production of DHPG is set forth in Scheme 7.

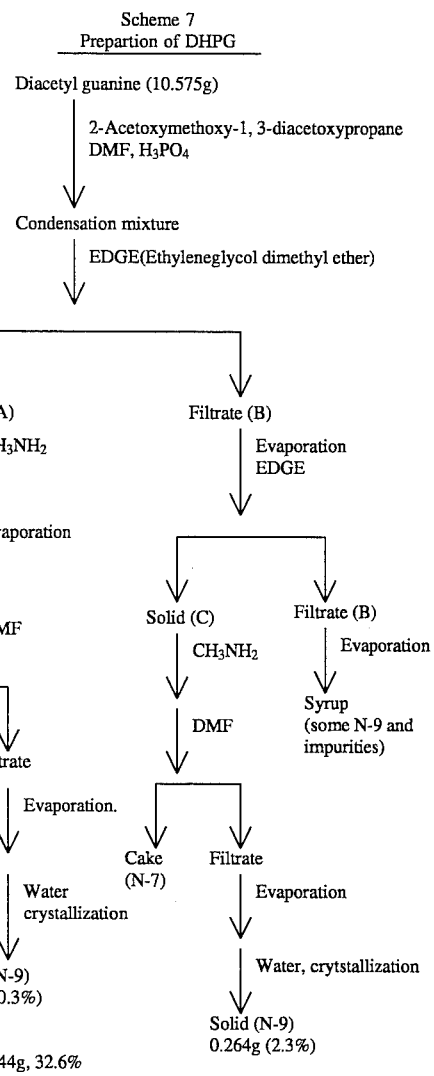

The condensation reaction was conducted using the procedure set forth in Example 7. After completion of the condensation reaction, the reaction solution was evaporated in vacuo to give a dark-brown syrup, which was triturated with 10 ml of ethylene glycol dimethyl ether and allowed to stand in refrigerator for 3 days.

The resulting yellow solid was collected on a funnel and washed with a small amount of ethylene glycol dimethyl ether and ether, to give a yellow solid (~10.1 g)(A) ($^1H$ NMR indicated that it was a mixture of compound 9 and 10). The filtrate and washings were combined and evaporated in vacuo to give a syrup (B).

The solid mixture (A) was gently refluxed in aqueous methylamine (40%, 100 ml) for 1.5 hours and then evaporated to dryness to give a solid (~6.54 g), which was triturated with 70 ml of DMF and stirred at room temperature overnight. The suspension was filtered. The filtrate was evaporated to dryness to give a yellow solid, which mainly contained $N^9$-isomer 12 based on NMR. The filter cake mainly contained N⁷-isomer 11. The crude product obtained from the filtrate was dissolved in 40 ml of water and decolorized with charcoal. A light-yellow solid product 12 (3.48 g, 30.3%) was obtained.

The syrup (B) was triturated with a minimum amount of ethylene glycol dimethyl ether again to give a yellow solid (C) (~2.4 g), which contained N⁷ and N⁹. The solid (C) was treated as described above and gave a yellow product N⁹ (0.264 g, 2.3%).

The combined yield of 12 was 3.744 g (32.6%).

Example 11

Solubilities of Compounds 5, 9, 10, and 11

The solubilities of compounds 5, 9, 10, and 11 were evaluated for the purpose of carrying out differential extraction or crystallization. The results are provided in Table 3.

TABLE 3

|  | Compound 9 | Compound 10 |
| --- | --- | --- |
| CHCl₃ | 1 g/19 ml | 1 g/20 ml |
| CH₂Cl₂ | 1 g/50 ml | 1 g/55 ml |
| Ethyl acetate | 1 g/125 ml | 1 g/138 ml |
| Acetone | 1 g/45 ml | 1 g/65 ml |
| Toluene | 1 g/>1600 ml | 1 g/11650 ml |

|  | Compound 5 | Compound 11 |
| --- | --- | --- |
| DMF | 1 g/60 ml | 1 g/80 ml |
| H₂O | 1 g/50 ml | 1 g/62 ml |
| EtOH | 1 g/>700 ml | 1 g/>800 ml |

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. A method for the preparation of an acyclic guanine nucleoside, comprising the step of reacting $N^2,N^9$-diprotected guanine with $CH_3C(O)OCH_2O(CH_2)_2OC(O)CH_3$ in the presence of acetic anhydride or propionic anhydride and phosphoric acid or polyphosphoric acid.

2. The method of claim 1, wherein the $N^2,N^9$-diprotected guanine is diacetylguanine.

3. The method of claim 2, wherein diacetylguanine is prepared by reacting guanine with acetic acid, acetic anhydride and phosphoric acid or polyphosphoric acid.

4. The method of claim 1, wherein the reaction product of $N^2,N^9$-diprotected guanine and $CH_3C(O)OCH_2O(CH_2)_2OC(O)CH_3$ is heated at a point in time in the reaction when the protected guanine has disappeared or almost disappeared from the reaction mixture to reduce or eliminate $N^7$-alkylated guanine.

5. The method of claim 1, further comprising carrying out the reaction in a solvent selected from the group consisting of toluene, xylene, cumeme, benzene, and ethylene glycoldiacetate.

6. The method of claim 1, wherein between 1.5 and 3 equivalents of $CH_3C(O)OCH_2O(CH_2)_2OC(O)CH_3$ to guanine is used.

7. The method of claim 1, wherein approximately 2 equivalents of $CH_3C(O)OCH_2O(CH_2)_2OC(O)CH_3$ to guanine is used.

8. The method of claim 1, wherein the reaction is carried out at a temperature ranging between 110°–130° C.

9. The method of claim 1, wherein the reaction is carried out at approximately 120° C.

10. The method of claim 1, further comprising recrystallizing the product of reaction in water.

11. The method of claim 1, further comprising recrystallizing the product of reaction in DMF.

12. The method of claim 1, wherein the guanine base is deprotected after the reaction.

13. The method of claim 1, in which acetic anhydride is used in the reaction.

* * * * *